United States Patent
Burge et al.

(10) Patent No.: US 11,413,185 B2
(45) Date of Patent: Aug. 16, 2022

(54) THERAPEUTIC TEXTILE ARTICLES AND METHODS OF USE

(71) Applicants: David L. Burge, Nashville, TN (US); Catherine M. Burge, Nashville, TN (US)

(72) Inventors: David L. Burge, Nashville, TN (US); Catherine M. Burge, Nashville, TN (US)

( * ) Notice: Subject to any disclaimer, the term of this patent is extended or adjusted under 35 U.S.C. 154(b) by 0 days.

(21) Appl. No.: 17/135,143

(22) Filed: Dec. 28, 2020

(65) Prior Publication Data

US 2021/0121321 A1 Apr. 29, 2021

Related U.S. Application Data

(63) Continuation of application No. 15/944,171, filed on Apr. 3, 2018, now Pat. No. 10,874,547.

(60) Provisional application No. 62/651,953, filed on Apr. 3, 2018, provisional application No. 62/530,626, filed on Jul. 10, 2017.

(51) Int. Cl.
*A61F 7/02* (2006.01)
*A61N 5/06* (2006.01)
*A61F 7/08* (2006.01)

(52) U.S. Cl.
CPC .............. *A61F 7/02* (2013.01); *A61F 7/08* (2013.01); *A41D 2400/10* (2013.01); *A41D 2400/32* (2013.01); *A61F 2007/0233* (2013.01); *A61F 2007/0266* (2013.01); *A61F 2007/0282* (2013.01); *D10B 2321/10* (2013.01); *D10B 2509/00* (2013.01)

(58) Field of Classification Search
None
See application file for complete search history.

(56) References Cited

U.S. PATENT DOCUMENTS

| | | | |
|---|---|---|---|
| 3,647,551 A | 3/1972 | Reed et al. | |
| 3,744,534 A | 7/1973 | Macnair et al. | |
| 4,675,915 A | 6/1987 | Sicillano | |
| 4,781,223 A | 11/1988 | McAliley et al. | |
| 4,865,906 A | 9/1989 | Smith | |
| 4,976,706 A * | 12/1990 | Aki | A61N 1/20 604/304 |
| 4,999,243 A * | 3/1991 | Maeda | D01D 5/30 139/420 A |
| 5,312,678 A | 5/1994 | McCullough, Jr. et al. | |
| 5,582,912 A | 12/1996 | McCullough et al. | |
| 5,700,573 A | 12/1997 | McCullough | |
| 5,782,790 A | 7/1998 | Allen | |
| 5,837,626 A | 11/1998 | McCullough | |
| 6,014,585 A | 1/2000 | Stoddard | |
| 6,316,102 B1 | 11/2001 | Sasaki | |
| 6,363,285 B1 * | 3/2002 | Wey | A61F 9/02 607/100 |
| 6,516,229 B1 | 2/2003 | Wey | |
| 6,860,122 B2 | 3/2005 | Goldberg | |
| 6,861,570 B1 | 3/2005 | Flick | |
| 7,223,376 B2 | 5/2007 | Panter et al. | |
| 7,291,762 B2 | 11/2007 | Flick | |
| 7,354,877 B2 | 4/2008 | Rosenberger et al. | |
| 7,428,772 B2 | 9/2008 | Rock | |
| 7,708,805 B2 | 5/2010 | Heine et al. | |
| 7,820,945 B2 | 10/2010 | Young | |
| 7,932,194 B2 | 4/2011 | Bader et al. | |
| 8,615,812 B2 | 12/2013 | Wojtowicz et al. | |

(Continued)

FOREIGN PATENT DOCUMENTS

| CN | 101660254 A | 3/2010 |
|---|---|---|
| CN | 101660254 B | 6/2011 |

(Continued)

OTHER PUBLICATIONS

Shanshan Shui, Xia Wang, John Y Chiang and Lei Zheng. Far-infrared therapy for cardiovascular, autoimmune, and other chronic health problems: Asystematic review. Experimental Biology and Medicine 2015; 240: 1257-1265. DOI: 10.1177/1535370215573391 (Year: 2015).*

"Cabric Inside." _TherMedic.com_ Mar. 3, 2017. _Internet Archive_. [https://web.archive.org/web/20170317100201/http://www.thermedic.com:80/technology/] (Year: 2017).*

Giulivi, Cecilia, et al. "Mitochndrial dysfunction in autism." JAMA 304.21 (2010: 2389-2396.

Loturco, Irineu, et al. "Effects of far infrared rays emitting clothing on recovery after an intense plyometric exercise bout applied to elite soccer players: a randomized double-blind placebo-controlled trial." Biology of Sport 33.3(2016): 277.

Tsai, Shang-Ru, and Michael R. Hamblin. "Biological effects and medical applications of infrared radiation." Journal of Photochemistry and Photobiology B: Biology 170 (2017): 197-207.

(Continued)

*Primary Examiner* — Bethany P Barham
*Assistant Examiner* — Peter Anthopolos
(74) *Attorney, Agent, or Firm* — Fox Rothschild LLP

(57) ABSTRACT

The present invention relates generally to therapeutic articles comprised of carbonaceous blend textile materials comprising yarns having about 25 to 100 weight % carbonaceous fiber and about 0 to 75 weight % fiber made of polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), and combinations thereof, or other fibers not listed that are capable of being made into yarn and textile fabrics that are knit, woven, or nonwoven, and wherein the fabric has a weight from about 3 oz/yd$^2$ to about 20 oz/yd$^2$. Also encompassed within this invention is a method for using therapeutic textile articles having carbonaceous blend textile materials of the present disclosure for treatment of humans and animals with developmental neurological disorders, central nervous system disorders, autoimmune disorders, cardiovascular disease, sleep disorders, anxiety disorders, pain management, and diabetes.

9 Claims, 5 Drawing Sheets

(56) References Cited

U.S. PATENT DOCUMENTS

| | | | |
|---|---|---|---|
| 8,652,975 | B1 | 2/2014 | Atkinson et al. |
| 8,935,813 | B2 | 1/2015 | O'Leary |
| 9,044,384 | B2* | 6/2015 | Canova .................... A61K 8/88 |
| 9,370,212 | B2 | 6/2016 | Zhu |
| 9,878,175 | B2 | 1/2018 | Goldberg |
| 2005/0262620 | A1 | 12/2005 | Li et al. |
| 2005/0266753 | A1 | 12/2005 | Fang et al. |
| 2006/0116043 | A1 | 6/2006 | Hope et al. |
| 2007/0134464 | A1 | 6/2007 | Schindzielorz et al. |
| 2007/0272385 | A1 | 11/2007 | Quigley et al. |
| 2008/0038973 | A1 | 2/2008 | Sasser et al. |
| 2009/0171423 | A1* | 7/2009 | Wada .................... A61N 5/0618 |
| | | | 607/88 |
| 2009/0177130 | A1 | 7/2009 | Wegher-Thompson |
| 2011/0016618 | A1 | 1/2011 | Li et al. |
| 2011/0104466 | A1* | 5/2011 | Atkinson ............... D01G 25/00 |
| | | | 428/219 |
| 2012/0100198 | A1 | 4/2012 | Li et al. |
| 2014/0152057 | A1 | 6/2014 | Truant et al. |
| 2015/0299904 | A1* | 10/2015 | Weiser ..................... D01F 1/10 |
| | | | 428/36.1 |
| 2015/0307670 | A1 | 10/2015 | McNamara et al. |
| 2016/0053411 | A1 | 2/2016 | Atkinson |
| 2016/0255891 | A1 | 9/2016 | Kimura et al. |
| 2016/0296558 | A1 | 10/2016 | Ko et al. |
| 2016/0353818 | A1* | 12/2016 | Psipsikas ............... D06M 11/36 |
| 2017/0035605 | A1* | 2/2017 | Estreicher ................ D02G 3/44 |
| 2018/0371648 | A1 | 12/2018 | Atkinson |

FOREIGN PATENT DOCUMENTS

| | | | |
|---|---|---|---|
| CN | 103251482 | A | 8/2013 |
| CN | 104856796 | A | 8/2015 |
| CN | 105996192 | A | 10/2016 |
| CN | 106263888 | A | 1/2017 |
| CN | 106562489 | A * | 4/2017 |
| FR | 3048854 | A1 | 9/2017 |
| GB | 2492534 | A | 1/2013 |
| GB | 2537168 | A | 10/2016 |
| TW | 201711650 | A | 4/2017 |
| WO | 2011050257 | A2 | 4/2011 |
| WO | 2013151753 | A1 | 10/2013 |

OTHER PUBLICATIONS

Vatansever, Fatma, and Michael R. Hamblin. "Far infrared radiation (FIR): Its biological effects and medical applications: Ferne Infrarotstrahlung: Biologische Effekte un medizinische Anwendungen." Photonics & Lasers in medicine 1.4 (2012): 255-266.

Screen shots of webpages from https://celliant.com published, Feb. 28, 2008, downloaded Oct. 8, 2019.

https://healthmatesauna.com/how-infrared-therapy-helps-children-with-autism, published Oct. 16, 2015.

Dr. Rachel West, http://www.drrachelwest.com/conditions/autism/, published Nov. 17, 2011.

http://www.mythermedic.com/mythermedic/index.php/cabric-inside.html, published Oct. 17, 2011.

http://industrial.tecgen.com/defining-fr-clothing-comfort/, published Sep. 15, 2014.

Harrison, Jill, Can Far-Infrared-Sauna Therapy Benefit Individuals on the Autism Spectrum, published Feb. 13, 2013.

International Preliminary Report on Patentability in co-pending PCT Appl. No. PCT/US2018/041262 dated Jan. 14, 2020.

"Biomats for Autistic Kids." DrSircus.com/light-heat/biomats-for-autistic-kids (published Jan. 24, 2014).

Hungs, Marcel, M.D., Ph.D., "Final Results of the Trial: Double blind, placebo controlled, crossover pilot trial on the effect of Optically Modified Polyethylene Terephthalate Fiber mattress covers on sleep disturbances in patients with chronic back pain: ClinicalTrials.gov Identifier: NCT00969540" from the Center for Sleep Medicine, Department of Neurology at the University of California, Irvine dated Feb. 15, 2010.

Gordon, Ian L., M.D., Ph.D., "Effect of Shirt with 42% Celliant Fiber on TCPO2 Levels and Grip Strength in Healthy Subjects" dated Jun. 30, 2009.

McClue, Graham, "Celliant (formerly Holofiber) Study of Thirteen (13) Healthy Subjects" dated Mar. 11, 2005.

Worobets, Jay T. et al., "Apparel with Far Infrared Radiation for Decreasing an Athlete's Oxygen Consumption during Submaximal Exercise," RJTA vol. 19 No. 3 2015.

Vatansever, Fatma and Hamblin, Michael R., "Far infared radiation (FIR): its biological effects and medical applications," Oct. 16, 2012, Photonics Lasers Med. Author manuscript, https://www.ncbi.nim.nih.gov/pmc/articles/PMC3699878/.

Cipolla MJ. The Cerebral Circulation, Chapter 5 Control of Cerebral Blood Flow, San Rafael (CA): Morgan & Claypool Life Sciences; 2009, https://www.ncbi.nlm.nih.gov/books/NBK53082/.

Antosova, Martina, Plevkova, Jana; Strapokova, Anna, and Buday, Tomas, Nitric Oxide—Important Messenger in Human Body, Open Journal of Molecular and Integrative Physiology, 2012, 2, 98-106; http://dx.doi.org/10.4236/ojmip.2012.23014 published online Aug. 2012 (http://www.SciRP.org/journal/ojmip/).

Extended European Search Report dated Dec. 3, 2021 in counterpart European Patent Application Ser. No. 18832931.2.

Chinese First Office Action dated Aug. 4, 2021 in counterpart Chinese Patent Application Ser. No. 201880058424.X.

https://farinfraredhealth.com/pages/far-infrared-clothing, printed from the Internet Archive, a/k/a Wayback Machine Khttps://archive.org/web/), having a screen capture date of Mar. 18, 2016.

http://diamondown.com/patented-technology/, printed from the Internet Archive, a/k/a Wayback Machine (https://archive.org/web/), having a screen capture date of Dec. 13, 2016.

http://www.thinknsa.com, printed from the Internet Archive, a/k/a Wayback Machine (https://archive.org/web/), having a screen capture date of Dec. 15, 2015.

http://www.thermedic.com/technology, printed from the Internet Archive, a/k/a Wayback Machine (https://archive.org/web/), having a screen capture date of Mar. 17, 2017.

http://www.thermedic.com/technology, downloaded Mar. 29, 2018.

Vatansever, Fatma and Hamblin, Michael R., "Far infrared radiation (FIR): its biological effects and medical applications," Oct. 16, 2012, Photonics Lasers Med. Author manuscript, https://www.ncbi.nim.nih.gov/pmc/articles/PMC3699878/.

"How Infrared Therapy Helps Children With Autism," Oct. 16, 2015, http://jama.jamanetwork.com/journal.aspx.

University of California—Davis Health System; "Children With Autism Have Mitochondrial Dysfunction, Study Finds", ScienceDaily,Nov. 30, 2010, www.sciencedaily.com/releases/2010/11/101130161521.htm.

Harrison J., Can Far-Infrared-Sauna Therapy Benefit Individuals on the Autism Spectrum?, Harrison J.; Health Freedom News, Winter 2012, pp. 15-17, http://www.thenhf.com/article?id-3620.

Cipolla MJ. The Cerebral Circulatin, Chapter 5 Control of Cerebral Blood Flow, San Rafael (CA): Morgan & Claypool Life Sciences; 2009, https://www.ncbi.nim.nih.gov/books/NBK53082/.

Antosova, Martina, Pelvkova, Jana; Strapokova, Anna, and Buday, Tomas, Nitric Oxide—Important Messenger in Human Body, Open Journal of Molecular and Integrative Physiology, 2012, 2, 98-106; http://dx.doi.org/10.4236/ojmlp.2012.23014 pbulished online Aug. 2012 (http://www.SciRP.org/journal/ojmip/).

International Search Report in counterpart PCT patent application No. PCT/US2018/041262 dated Sep. 19, 2018.

Fox, Cathy Burge: Faces of Nashville, StyleBlueprint, Aug. 9, 2015 [retrieved on Aug. 22, 2018]. Retrieved from the Internet: <URL: https://web.archive.org/web/20150916173545/https://styleblueprint.com/nashville/everyday/cathy-burge-faces-nashville/>entire document.

Chinese Final Rejection of Application dated Feb. 28, 2022 in counterpart Chinese Patent Appl. No. 201880058424.X.

Zhu Tianshen, "Talks of old professors in Donghua University", Shanghai, Donghua University Press, Oct. 31, 2013, p. 106.

Yao, Dingshan, "Magnet-Far-Infrared Ray Health", China Textile University Press, Feb. 28, 2005, p. 131.

(56) References Cited

OTHER PUBLICATIONS

Xiao, Ming, Liang Zhongua, Wu Ruixiong, "Fashion Household Electrical Appliances: Structures/Use/Maintenance", Science and Technology Literaure Press, Aug. 31, 1995, p. 248.
Chen Dongsheng, Gan Yingjin, "New Clothing Materials", China Light Industry Press, Jan. 31, 2001.
Wang Jianguo, "New Knowledge Library: Fiber World", Anhui Normal University Press, Apr. 30, 2012, pp. 79-80.

* cited by examiner

THERAPEUTIC TEXTILE ARTICLES AND METHODS OF USE

This application claims benefit from U.S. Nonprovisional patent applicant Ser. No. 15/944,171, filed Apr. 3, 2018, which claims benefit under 35 U.S.C. Section 119(e) from U.S. Provisional Patent Application Ser. No. 62/530,626, filed Jul. 10, 2017 and U.S. Provisional Patent Application Ser. No. 62/651,953 filed Apr. 3, 2018, the entirety of all of the foregoing applications being hereby incorporated by reference.

TECHNICAL FIELD

The present invention relates generally to therapeutic articles, such as clothing, blankets, wraps, etc., constructed using a nonconductive carbonaceous fiber blend textile and methods of treatment of humans and animals using such therapeutic articles.

BACKGROUND

Many adults and children suffer with Sensory Processing Disorder (also known as "sensory integration dysfunction"), autistic spectrum disorders (also known as "Pervasive Development Disorders (PDDs)), attention deficit disorders (ADD), including attention deficit hyperactivity disorder (ADHD), anxiety disorders, emotional and behavioral disorders, sensory-based learning disorders, and other medical disorders including but not limited to central nervous system disorders, autoimmune disorders, cardiovascular disease, sleep disorders, anxiety disorders, pain management, and diabetes. Treatment for such disorders and conditions meets with varying degrees of success and may produce undesirable side effects and/or unintended consequences.

For example, anxiety can be a serious problem for many people on the autism spectrum, and such anxiety can take the form of one or more disorders, including panic disorder and phobias. Currently, medications are generally unavailable which have been approved by the Federal Drug Administration (FDA) expressly for the treatment of anxiety in children, adolescents, and adults with autism. However, certain therapies exist for treatment of children with autism, including Applied Behavior Analysis (ABA). ABA therapy typically systematically applies interventions based on learning theory to improve socially significant behaviors. While ABA may improve the abilities of children with autism to learn and develop, in certain cases, it may not be fully effective, especially with regard to young children who may not be able to effectively express their feels of anxiety. Anxious children, for example, may insist on even more routines, have more trouble sleeping, have "meltdowns" or temper tantrums, avoid or withdraw from social situations, rely more on rituals and obsessions, stimulate themselves by rocking, spinning or flapping hands, and/or engage in self-harm by head banging, biting, or scratching.

In cases where a child or adult with autism spectrum disorder (ASD) experiences a multitude of sensory challenges, sensory processing integration issues, or sensory processing disorder (SPD), issues may arise with temperature regulation. A person with autism may not be able to adequately adapt to changing temperatures and/or may not feel temperatures in the way a neuro-typical person does. Accordingly, living with temperature regulations issues can put such a person in a constant state of discomfort, including hypersensitivity to hot and cold temperatures, which may make physical activities more dangerous. Further, in cases where a person has a lack of sensitivity to hot and cold temperatures, such condition may also make physical activities more dangerous.

A significant number of children with ASD are thought to have clinically significant symptoms of ADD/ADHD, and such incidents may be significantly higher than the incidents in the general population. ADHD may be characterized by developmentally inappropriate levels of inattention, impulsivity, and/or hyperactivity. Autistic children with ADD/ADHD may face greater impairments and have more difficulty learning and socializing as compared to children with ASD only. Given ASD may be characterized by impairments in communication, social reciprocity, and repetitive behaviors, when the combined symptoms of ADD/ADHD remain untreated, positive outcomes are decreased.

It has been estimated that between forty and eighty percent of children with autism have difficulty sleeping. Sensory issues may add to sleep disturbances common to children with autism, and some research indicates that for children with autism, there is a connection between lack of sleep, aggression, hyperactivity, increased behavior problems, and poor learning. Further, the lack of a good night's sleep can affect not only the child, but others in the child's family and/or immediate care group.

Moreover, certain people with autism are able to tolerate extreme cold and seem relatively insensitive to pain. Paradoxically, they may experience pain from idiosyncratic sources that may not bother a neuro-typical person, but struggle to communicate it. It is thought that sensory challenges may affect up to 70% of people with autism, and in certain research, sensory sensitivity may be more strongly associated with pain than anxiety. Children hypersensitive to sounds, smell, tactile and other stimuli may tend to have more abdominal pain at the outset, and may also be likely to develop new abdominal pain. Unable to express themselves, some children may turn their frustration outward, or even inward against themselves. Some evidence seems to indicate that the very behaviors interpreted as high tolerance to pain, such as head banging or hand biting, may in fact be signs that the individual is in agony.

Thus, improved treatment techniques, articles and methods for treating developmental neurological conditions and other conditions are desired.

SUMMARY

In light of the foregoing discussion, the present invention relates generally to therapeutic wearable textile articles, such as clothing, and other articles for placing on or against a patient (which could be human or animal), such as blankets, sheets, bedding, wraps, etc., constructed using nonconductive, nonactivated carbonaceous fiber blend textiles and methods of treatment of patients using such therapeutic textile material and articles.

Generally, an implementation of the present disclosure includes a method of treatment of a patient having a developmental neurological disorder, including providing a textile article comprising a carbonaceous fiber blend textile material, and at least partially covering the patient with a textile article comprising a carbonaceous fiber blend textile material in order to yield a therapeutic benefit to the patient. More specifically, the method may include the carbonaceous fiber blend textile material comprising yarns including about 25 to 100 weight % nonconductive, nonactivated carbonaceous fiber and about 0 to 75 weight % fiber made from a group consisting of polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA). Another implementation of the method could include the carbonaceous fiber blend textile material comprising fibers capable of being made into yarn and knit, woven, or used in nonwovens, and wherein the carbonaceous fiber blend textile material has a weight from about 3 oz/yd$^2$ to about 20 oz/yd$^2$.

In another implementation of the present disclosure, a textile article is provided suitable for use in treating a patient having a developmental neurological disorder. Such textile article comprises a carbonaceous fiber blend textile material comprises yarns consisting essentially of about 25 to 100 weight % nonactivated carbonaceous fiber and about 0 to 75 weight % fiber made from a group consisting of polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), wherein the carbonaceous fiber blend textile material comprises fibers capable of being made into yarn and knit, woven, or used in nonwovens, and wherein the carbonaceous fiber blend textile material has a weight from about 3 oz/yd$^2$ to about 20 oz/yd$^2$.

In another implementation of the present disclosure, method is disclosed for treating a user with a neurological disorder, comprising providing a textile article including 5 to 100 weight % carbonaceous fiber, and 0 to 75 weight % blending fiber at least partially covering the user with the textile article; absorbing with the textile article convective and radiant energy generated by the user; and emitting back to the user from the textile article at least 50% of convective and radiant energy received from the user when the textile article is in proximate contact with the user, wherein the emitted energy is in the far infrared spectrum, and, wherein the emitted energy provides a therapeutic benefit to the user. In another implementation, the method further includes the carbonaceous fiber being an oxidized polyacrylonitrile fiber that absorbs convective and radiant energy generated by the user, and responsively emits the absorbed energy in the far infrared spectrum, and, optionally, wherein the oxidized polyacrylonitrile fiber is about 30 to 70 weight %, and the blending fiber is about 30 to 70 weight %.

A further implementation includes a method wherein the carbonaceous fiber is an oxidized polyacrylonitrile fiber that absorbs convective and radiant energy from an environment, and responsively emits the absorbed energy in the far infrared spectrum.

A further implementation may include the blending fiber being an apparel fiber comprising polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), or any combination thereof, and optionally, further comprising evaporating moisture present between the user and the textile article using the emitted energy and/or wherein the neurological disorder is autism and/or wherein the neurological disorder is pediatric autism.

Yet another implementation includes a method of controlling and reducing net perspiration demand of a user comprising providing a textile article having 25 to 100 weight % carbonaceous fiber, and 0 to 75 weight % blending fiber; at least partially covering the user with the textile article; and emitting back to the user from the textile article at least 50% of convective and radiant energy received from the user by the textile article in the form of far infrared energy when the textile article is in proximate contact with the user; and evaporating moisture present between the user and the textile article with the emitted energy. Such method may include the carbonaceous fiber being an oxidized polyacrylonitrile fiber that absorbs convective and radiant energy generated by the user, and responsively emits the generated energy in the far infrared spectrum and/or the carbonaceous fiber being an oxidized polyacrylonitrile fiber that absorbs convective and radiant energy from an environment, and responsively emits the absorbed energy in the far infrared spectrum. Another implementation includes the carbonaceous fiber being an oxidized polymeric fiber and is about 30 to 70 weight %; and the blending fiber is about 30 to 70 weight %.

In another implementation of the present disclosure, the blending fiber is an apparel fiber comprising polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), or any combination thereof.

A further implementation includes a textile article suitable for use in treating a user having a neurological disorder, the textile article comprising 25 to 100 weight % carbonaceous fiber; and 0 to 75 weight % blending fiber. Such textile article could include the carbonaceous fiber being an oxidized polyacrylonitrile fiber that absorbs convective and radiant energy generated by the user, and responsively emits the absorbed energy in the far infrared spectrum and/or wherein the carbonaceous fiber is an oxidized polyacrylonitrile fiber that absorbs convective and radiant energy from an environment, and responsively emits the absorbed energy in the far infrared spectrum and/or wherein the carbonaceous fiber is an oxidized polymeric fiber and is about 30 to 70 weight %; and the blending fiber is about 30 to 70 weight %. Optionally, the textile article includes the blending fiber being an apparel fiber comprising polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), or any combination thereof. In a still further implementation, the neurological disorder is autism and/or pediatric autism.

In another implementation, the textile article emits at least 50% of convective and radiant energy absorbed from the user when the textile article is in proximate contact with the user and/or the emitted energy is in the far infrared spectrum. Optionally, the textile article fibers are combinable into yarn and knit, woven, or nonwoven forms, and wherein the textile article has a fabric weight from about 3 oz/yd$^2$ to about 20 oz/yd$^2$.

Additional information concerning the formation and use of nonactivated carbonaceous fibers is disclosed in U.S. Patent Application Publication Nos. 20110104466 (published May 5, 2011) and 20160053411 (published Feb. 25, 2016) of Atkinson, both being entitled, "Blended Fiber Yarns and Fabrics Including Oxidized Polymeric Fibers;" in U.S. Pat. No. 7,223,376 (issued May 29, 2007), to Panter, et al., entitled, "Apparatus and Method for Making Carbon Fibers"; in U.S. Pat. No. 8,652,975 (issued Feb. 18, 2014), to Atkinson, et al., entitled, "Flame Resistant Fabric"; in U.S. Patent Application Publication No. 20110016618 (published Jan. 27, 2011) of Li, et al., entitled, "Protective Garment System Having Activated Carbon Composite with Improved Absorbency;" in U.S. Pat. No. 5,700,573 (issued Dec. 23, 1997) of McCullough, entitled, "Flexible Biregional Carbonaceous Fiber, Articles Made from Biregional Carbonaceous Fibers, and Method of Manufacture;" and in U.S. Pat. No. 5,837,626 (issued Nov. 17, 1998), also of McCullough, entitled, "Ignition Resistant or Fire Blocking Composite," the entirety of the foregoing U.S. patents and patent applications being hereby incorporated herein by reference.

More specifically, the present invention is directed to the development of textile articles for adults and children with Sensory Processing Disorder (also known as "sensory integration dysfunction"), autistic spectrum disorders (also known as "Pervasive Development Disorders (PDDs)), attention deficit disorders (ADD), including attention deficit hyperactivity disorder (ADHD), anxiety disorders, emotional and behavioral disorders, sensory-based learning disorders, and other developmental neurological disorders.

Generally, one implementation of the present disclosure includes use of textile articles including yarns that naturally absorb and return to the body of the wearer the wearer's own healing and calming far infrared energy (FIR). Invisible to the naked eye, far infrared energy is found at the opposite end of the visible light spectrum from ultraviolet (UV) energy and is believed to promote good health. Humans absorb safe, healing far infrared energy from the sun (FIG. 6). The healing rays heat the muscles, nerves, and blood vessels, and this heating can result in benefits such as pain relief, reduced anxiety, and restful sleep.

Documented benefits of FIR by the National Institute of Health (NIH) include anxiety reduction, fatigue reduction, pain management, faster healing, improved sleep, cancer cell inhibition, cellulite reduction, detoxification, strengthening the immune system, anti-aging, and improved cardiac and vascular function. See, for example the research results found at https://www.ncbi.nlm.nih.gov/pmc/articles/PMC3699878/, the entirety of which is hereby incorporated by reference.

Far infrared energy also promotes creation of nitric oxide. The action of nitric oxide was not discovered until about 1991. Subsequently, three Pharmacologists, Robert F. Furchgott, Louis J. Ignarro, and Ferid Murad won the Nobel Prize in 1996 for "for their discoveries concerning nitric oxide as a signaling molecule in the cardiovascular system." See, for example, the research results found at "The Nobel Prize in Physiology or Medicine 1998," Nobelprize.org, Nobel Media AB 2014, Web. 10 Jul. 2017, http://www.nobelprize.org/nobelprizes/medicine/laureates/1998/, the entirety of the foregoing research being hereby incorporated herein by reference.

A study published in the Journal of the American Medical Association (JAMA) by University of California-Davis found that children with autism often show the inability to produce cellular energy as compared to children without autism. The study also found that cumulative damage and oxidative stress in mitochondria, the body's life sustaining process and cell energy producer, can affect both the arrival and difficulty of autism, leading to a strong statistical relation between autism and mitochondrial defects. Far infrared energy for individuals with autism improves the body's ability to trigger the release of nitric oxide (NO) from the endothelial lining of the blood vessels. Nitric oxide helps preserve blood-vessel elasticity and enhances blood circulation. This has significant implications, because optimal blood circulation is a key factor for healing numerous health issues, but also especially for people with autism. See, for example the research results found at Journal of the American Medical Association, "How Infrared Therapy Helps Children With Autism," Oct. 16, 2015, http://jama.jamanetwork.com/journal.aspx (See also https://healthmatesauna.com/how-infrared-therapy-helps-children-with-autism/); University of California—Davis Health System; "Children with autism have mitochondrial dysfunction, study finds", ScienceDaily, 30 Nov. 2010, www.sciencedaily.com/releases/2010/11/101130161521.htm; Harrison J., Can far-infrared-sauna therapy benefit individuals on the autism spectrum?, Harrison J.; Health Freedom News, Winter 2012, pp. 15-17, http://www.thenhf.com/article?id=3620; Dr. Rachel West, http://www.drrachelwest.com/conditions/autism/; Cipolla M J. The Cerebral Circulation, Chapter 5 Control of Cerebral Blood Flow, San Rafael (Calif.): Morgan & Claypool Life Sciences; 2009, https://www.ncbi.nlm.nih.gov/books/NBK53082/; and Antosova, Martina, Plevkova, Jana; Strapokova, Anna, and Buday, Tomas, "Nitric Oxide—Important Messenger in Human Body, Open Journal of Molecular and Integrative Physiology, 2012, 2, 98-106, the entirety of the foregoing research results being hereby incorporated herein by reference.

Cerebral hypo-perfusion is simply decreased blood flow to the brain (FIG. 7), and numerous medical studies have demonstrated cerebral hypo-perfusion in children with autism. The diminished blood flow can be seen with a correlation to many core autistic symptoms/behaviors. For example, when the thalamus has hypo-perfusion, the results are repetitive, self-stimulatory, and unusual behaviors may be presented by individuals with autism.

Additionally, bones and tissues of the body use conduction, convection, evaporation, and radiation to move the heat energy outward (FIG. 8).

In one implementation of the present disclosure, textile material includes functional fibers and/or yarns consisting essentially of about 25 to 100 weight % nonactivated, nonconductive, fire resistant carbonaceous fiber and about 0 to 75 weight % fiber made of polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), and combinations thereof, or other fibers not listed that are capable of being made into yarn and textile fabrics that are knit, woven, or used in nonwovens, and wherein the fabric has a weight from about 3 oz/yd$^2$ to about 20 oz/yd$^2$.

A working theory as to the efficacy of treating symptoms of autism with carbonaceous fiber blend textile material appears to be that at least one implementation of carbonaceous fiber blend textile material regulates patient body temperature by reflecting perhaps up to approximately 90% of the body's radiant energy.

Fabrics made from these yarns exhibit a combination of properties that make them have been shown in limited testing to be strongly preferred by wearers, particularly compared to fabrics without carbonaceous fibers. More particularly, in addition to inherent temperature regulation properties, these novel yarns yield fabrics capable of reflecting the body's radiant energy stimulating blood flow that induces calming effects, pain relief, and behavior changes especially with those individuals on the autism spectrum or sensory processing spectrum. Positive behavior changes for individuals on the autism spectrum or sensory processing spectrum observed include, but are not limited to: reduced anxiety; improved calm; reduced meltdowns; reduced aggression; improved sleep; improved comfort in sports and other physical activities; reduced danger of hypothermia and hyperthermia; improved focus and concentration; reduce pain sensitivity; reduced self-harming behaviors; improved Applied Behavior Analysis (ABA) and learning; and/or improved communication.

Implementations of the present disclosure include attractive, comfortable, and sensory-friendly garments, namely, shirts, pants, and underwear, and also sensory-friendly sleepwear for children and adults. Implementations also include blankets, such as medical, personal, and veterinary blankets in a wide range of sizes and weights, including without limitation blankets for infant care, medical care, and home use, and veterinary applications for blankets and surgery. Additional more specific implementations include clothing for athletics, military, emergency personnel, search and rescue personnel, hunting, skiing, daily wear, patient care bandages and garments, outwear including coats, gloves, and hats, etc.

Other objects, advantages, and features of the current invention will occur to those skilled in the art. Thus, while the invention will be described and disclosed in connection with certain preferred implementations and procedures, such implementations and procedures are not intended to limit the scope of the current invention. Rather, it is intended that all such alternative embodiments, procedures, and modifications are included within the scope and spirit of the present disclosure.

BRIEF DESCRIPTION OF THE DRAWINGS

Figure 1:
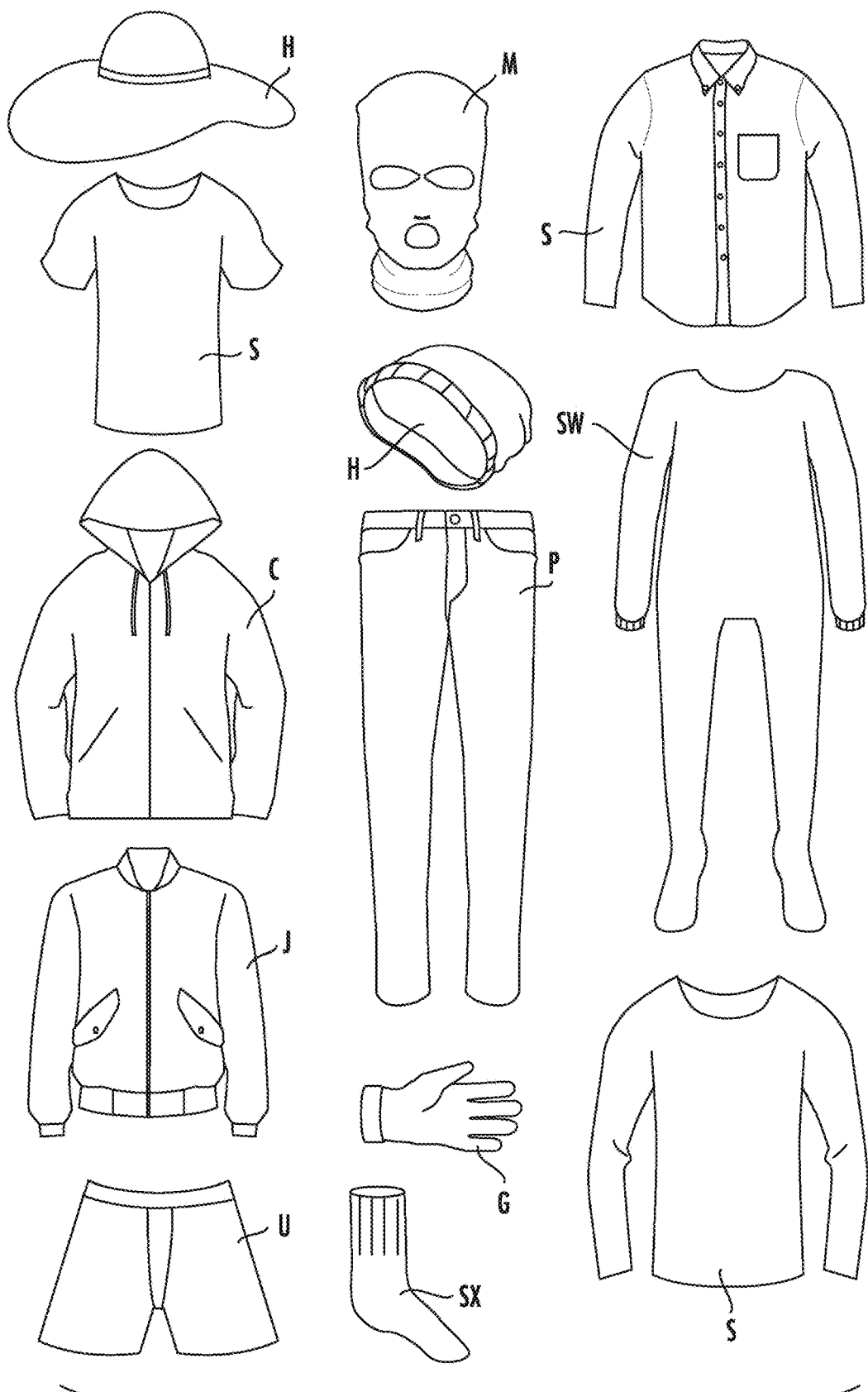
Figure 2:
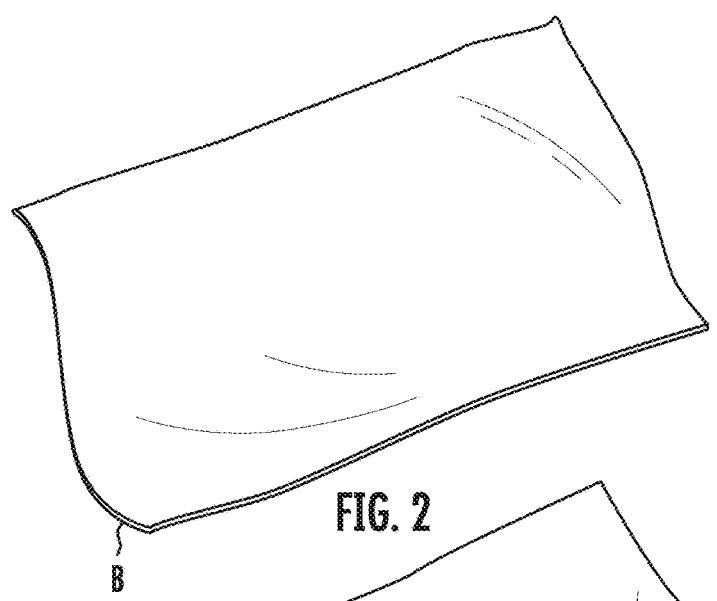
Figure 3:
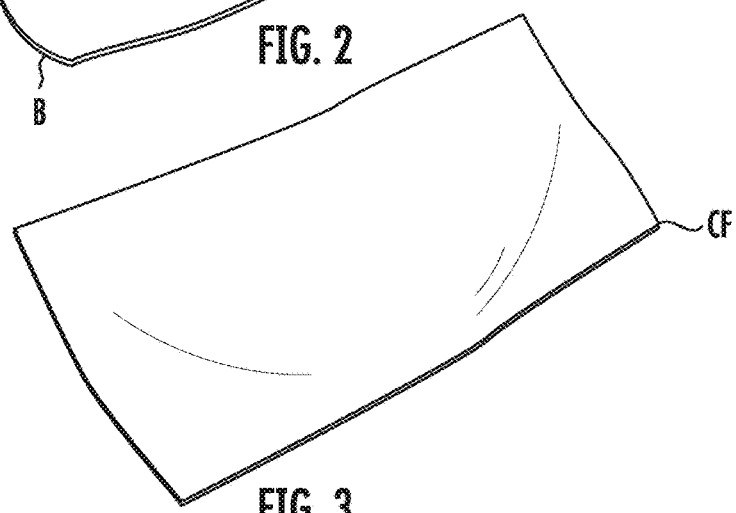
Figure 4:
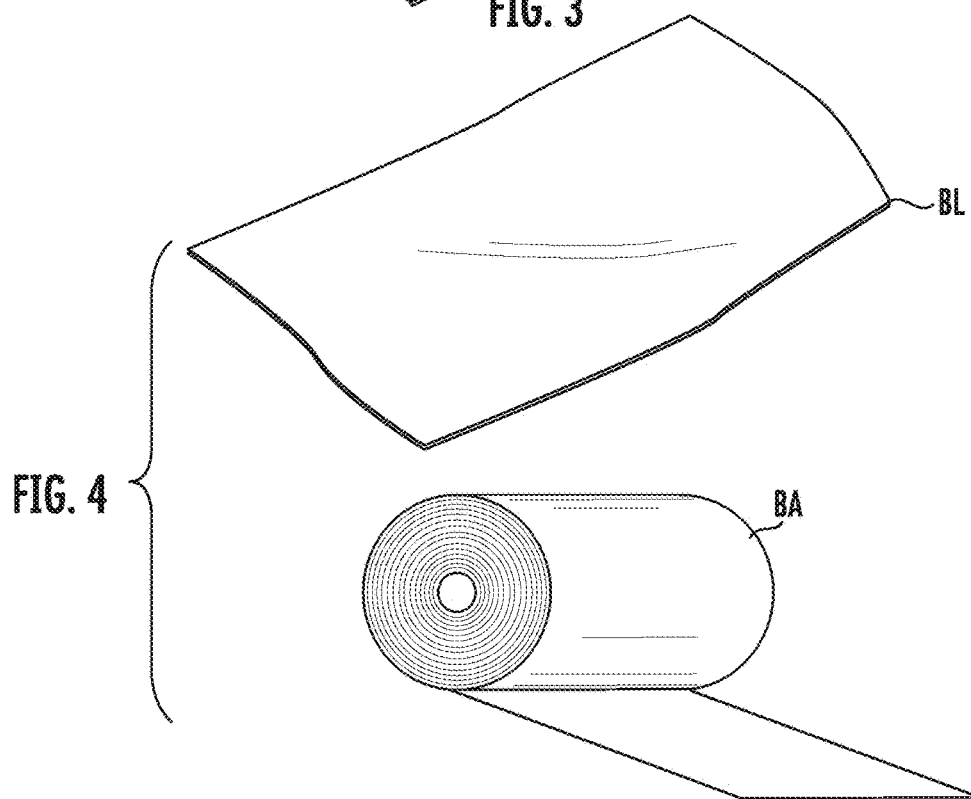
Figure 5:
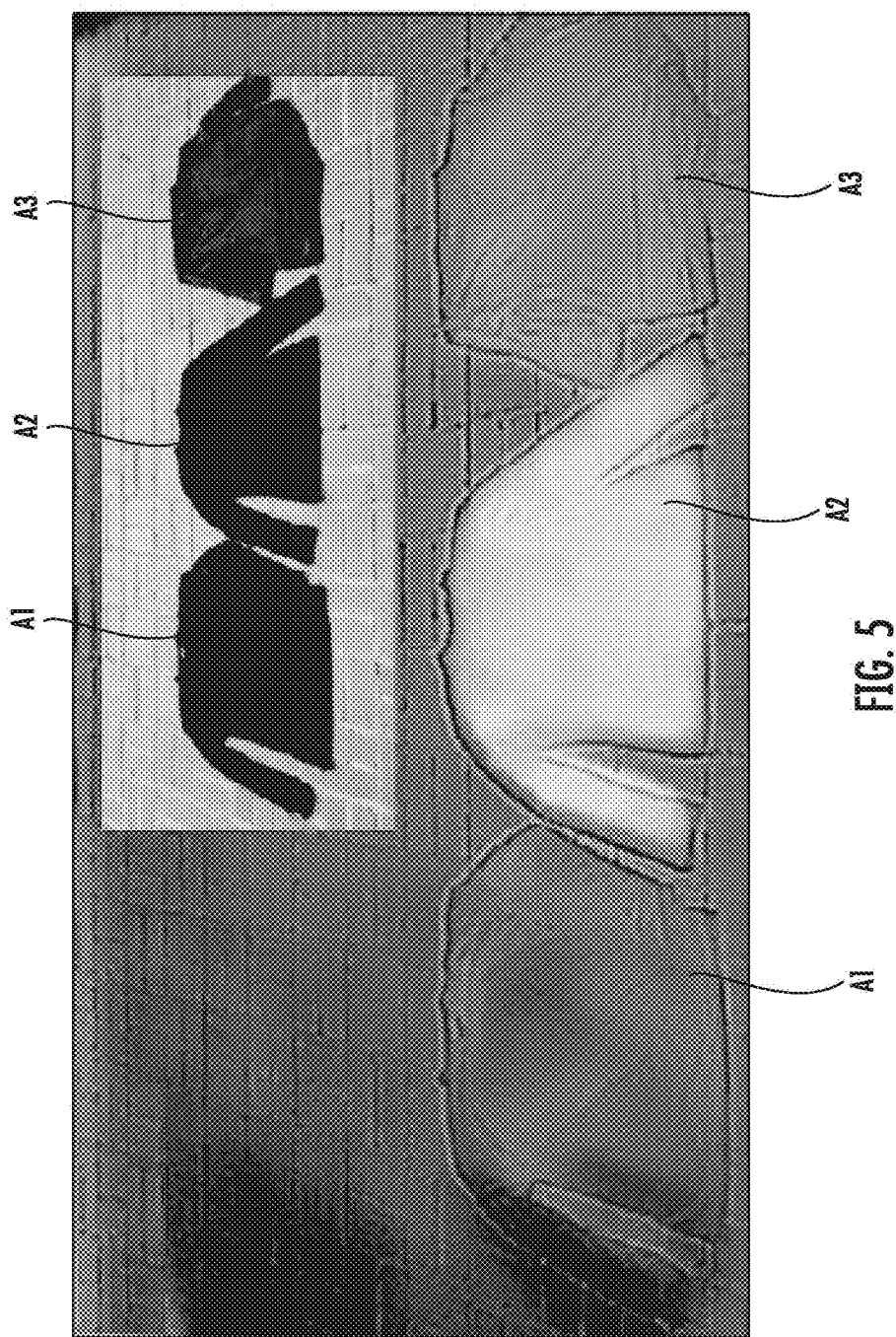
Figure 6:
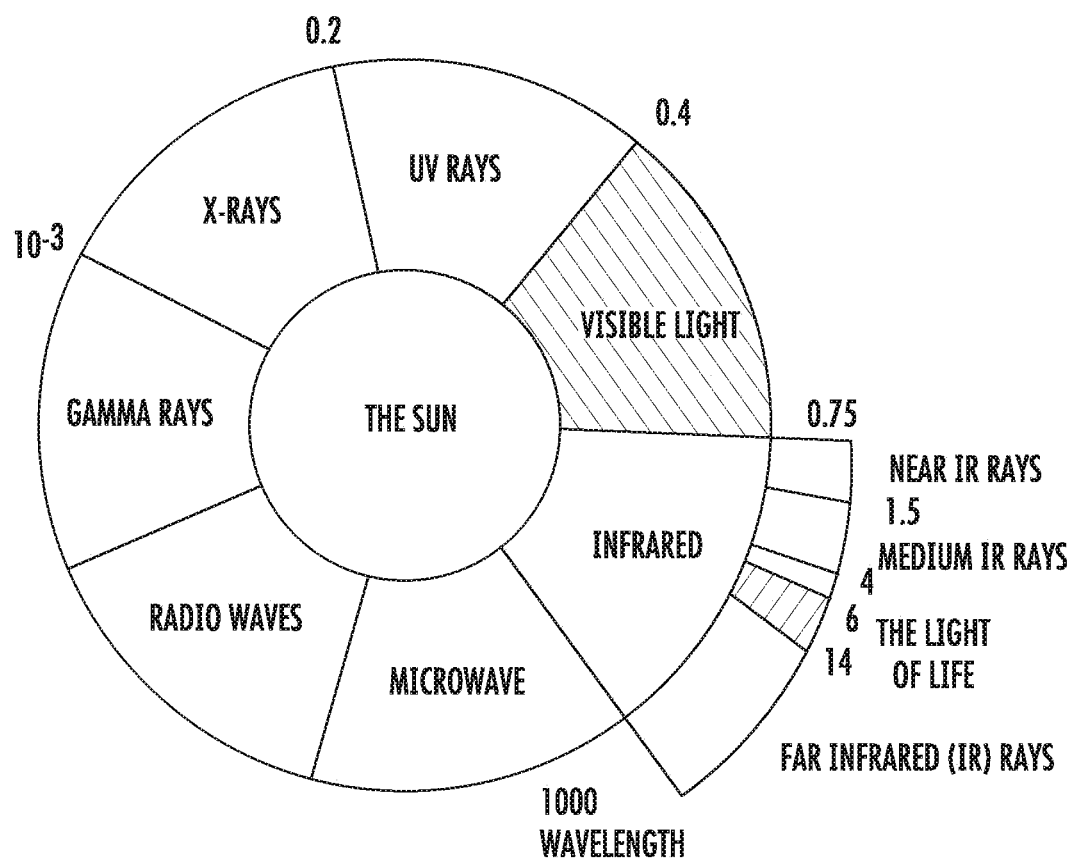
Figure 7:
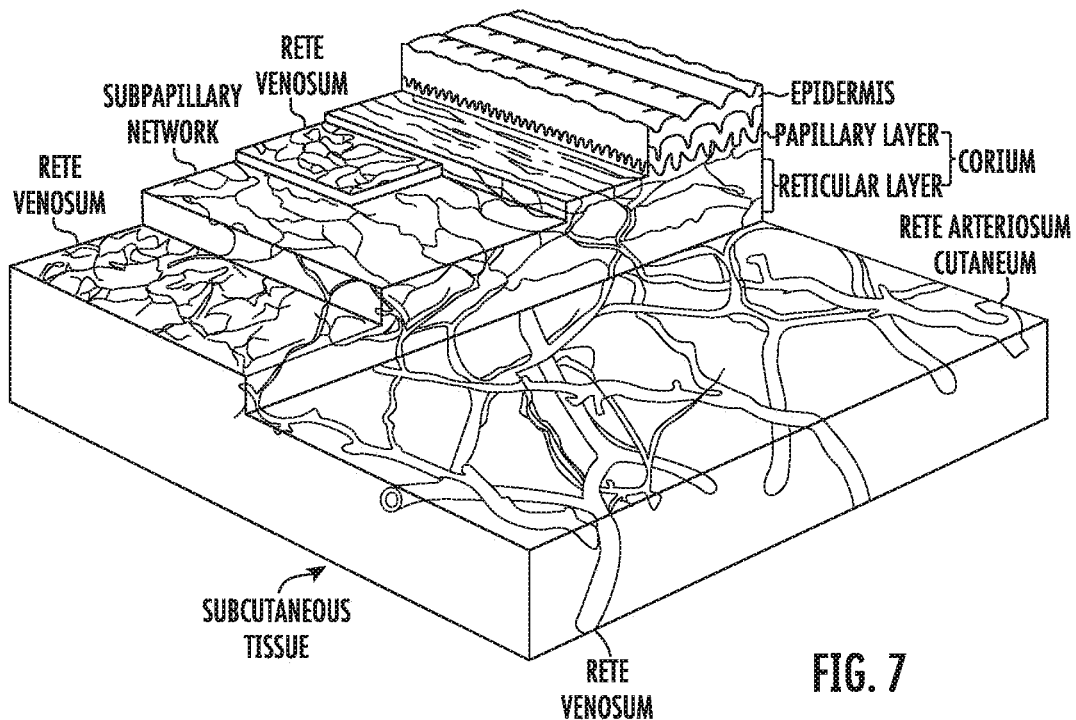

Having thus described exemplary aspects of the disclosure in general terms, various objects, features, and attendant advantages of the disclosed concepts will become more fully appreciated as the same becomes better understood when considered in conjunction with the accompanying drawings, which are not necessarily drawn to scale, in which like reference characters designate the same or similar parts throughout the several views, and wherein:

FIG. 1 is a schematic view of various examples of implementations of articles of clothing as discussed herein;

FIG. 2 is a schematic view of an example implementation of a blanket as discussed herein;

FIG. 3 is a schematic view of an example implementation of a textile as discussed herein;

FIG. 4 is a schematic view of an example of implementations of medical articles as discussed herein; and FIG. 5 is an image of forward looking infrared (FLIR) thermal imaging of clothing articles exposed to sunlight emitting varying amounts of FIR, with clothing article A2 being made from fabric made in accordance with the present disclosure;

FIG. 6 is a diagramatic representation of various ultraviolet energy characterizations;

FIG. 7 is a diagramatic representation of components of the brain; and

Figure 8:
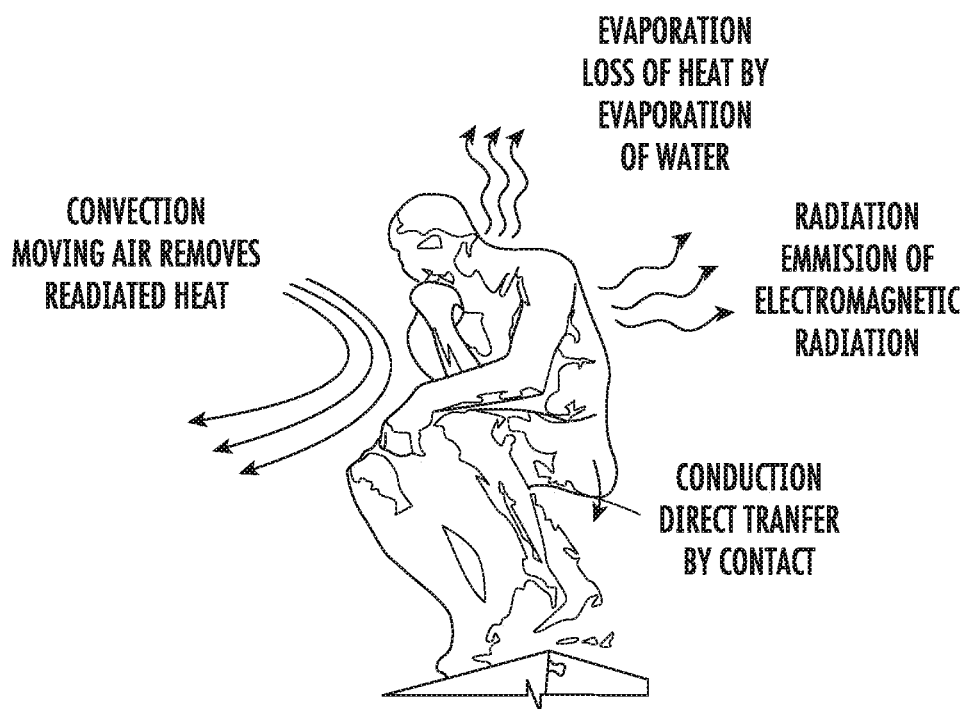

FIG. 8 is a diagramatic representation of the conduction, convention, evaporation, and radiation of energy outward from the body.

DETAILED DESCRIPTION

Carbonaceous fiber blend textile articles are provided which have therapeutic properties for use in connection with treatment of, among other conditions and diseases, developmental neurologic disorders, which are created without significantly compromising the textile hand (or feel) of the textile or the surface appearance of the textile.

The textile, or fabric, of the current invention can be formed from fibers such as synthetic fibers, natural fibers, or combinations thereof. Synthetic fibers include, for example, polyester, acrylic, polyamide, polyolefin, polyaramid, polyurethane, regenerated cellulose, and blends thereof. Natural fibers include, for example, wool, cotton, flax, and blends thereof.

The fabric can be formed from fibers or yarns of any size, including microdenier fibers and yarns (fibers or yarns having less than one denier per filament). Furthermore, the fabric may be partially or wholly comprised of multicomponent or bi-component fibers or yarns which may be splittable along their length by chemical or mechanical action. The fabric may be comprised of fibers such as staple fiber, filament fiber, spun fiber, or combinations thereof.

The fabric of the present disclosure may be of any variety, including but not limited to, woven fabric, knitted fabric, nonwoven fabric, or combinations thereof. They may optionally be colored by a variety of dyeing techniques, such as high temperature jet dyeing with disperse dyes, thermosol dyeing, pad dyeing, transfer printing, screen printing, or any other technique that is common in the art for comparable, equivalent, traditional textile products. If yarns or fibers are treated by the process of the current invention, they may be dyed by suitable methods prior to fabric formation, such as, for instance, by package dyeing or solution dyeing, or after fabric formation as described above, or they may be left undyed.

One potentially preferred, non-limiting yarn is in one implementation of the present disclosure, includes textile material having functional fibers and/or yarns consisting essentially of about 25 to 100 weight % nonconductive, nonactivated, fire resistant carbonaceous fiber and about 0 to 75 weight % fiber made of polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), and combinations thereof, or other fibers not listed that are capable of being made into yarn and textile fabrics that are knit, woven, or used in nonwovens, and wherein the fabric has a weight from about 3 oz/yd$^2$ to about 20 oz/yd$^2$.

If a dyed fabric is desired, dyeing may be accomplished by any technique known to those skilled in the art, such as, for example, by solution dyeing the fiber used to make the fabric, dyeing the formed fabric in a jet dye machine, dyeing the formed fabric using a continuous process dyeing range, or any combination thereof. Additionally, the fabric may also be subjected to various face-finishing processes prior to screen printing. In one aspect of the present invention, the process of the current invention requires no special equipment; standard textile equipment may be employed.

Implementations of the present disclosure include comfortable and sensory friendly garments, such as shirts S, pants P, and underwear U, coats C, headwear H, masks and balaclavas M, jackets J, gloves G, socks SX, and also sensory friendly sleepwear SW for children and adults (FIG. 1). Implementations also include blankets B (FIG. 2), such as medical, personal, and veterinary blankets in a wide range of sizes and weights, such as: blankets for infants care, medical care, and home use; and veterinary applications for blankets and surgery. Additional more specific implementations include of carbonaceous fiber blend material CF (FIG. 3) of the present disclosure could include clothing for athletics, hunting, skiing, daily wear, patient care blankets BL and bandages BA (FIG. 4) and garments, outwear including coats, gloves, and hats, etc.

The following examples illustrate various embodiments of the present invention but are not intended to restrict the scope thereof.

EXAMPLE

In one non-limiting example, in an independent research study, children with autism ages 2 to 10 years old wore shirts made with textile material of the present invention for fifty (50) days. Such textile material included 46 weight % polyester, 32 weight % carbonaceous, 14 weight % Modal, and 8 weight % Lycra.

Teachers and parents of such children observed the following behavior changes:

| | |
|---|---|
| Children found the shirt comfortable | 100% |
| Reduced hyperactivity | 66% |
| Improved ability to focus | 50% |
| Reduced anxiety | 50% |
| Positive impact on child's behavior | 43% |
| Improved ABA responses | 33% |

In one implementation of textile material of the present disclosure, functional fibers are 100% FIR absorbers and emitters driven by body heat internally or the sun externally. Yarn blend ranged from 30% to 70% FIR fibers.

It has been demonstrated that fabric made in accordance with the present disclosure emit significantly more FIR than other fabrics, as shown in FIG. 5, wherein the results of comparisons of clothing articles A1, A2, and A3 exposed to sunlight emit varying amounts of FIR, with clothing article A2 being made from fabric made in accordance with the present disclosure. Note that using a FLIR thermal imaging system, the brighter/lighter the image appears, the more the FIR emissions, and that clothing article A2 is noticeably brighter than the other to clothing articles A1 and A2.

In contrast to conventional wicking fibers, where moisture is drawn from the skin and transported to the outer surface of the garment for evaporation, fabrics made from at least one implementation of a carbonaceous fiber blend textile material of the present disclosure drive evaporation inside the fabric using the body's retained radiant energy. Once the needed heat has been released, such carbonaceous fiber blend textile material fibers will also use the body's heat to dramatically reduce or eliminate "sweat chills". The effect is that fabrics made with such carbonaceous fiber blend become temperature regulating and extremely comfortable to wear.

In addition to temperature regulating properties, fabrics made from at least one implementation of a carbonaceous fiber blend textile material of the present disclosure also elicit positive responses for medical conditions impacted by surface blood flow. Documentation supports the benefits of compression that mechanically stimulates the surface vascular system. Fabrics made from at least one implementation of a carbonaceous fiber blend textile material of the present disclosure may also stimulate the surface vascular system. With or without compression, such fabrics improve vascular circulation and increase comfort.

In at least one example, fabrics made from at least one implementation of a carbonaceous fiber blend textile material of the present disclosure have had a positive impact on the physiology and behavior of individuals with Autism, Sensory Processing Disorder, ADD/ADHD, diabetes, and menopause. A working hypothesis or theory is that the body's radiant energy, specifically far infrared wavelengths between 6 and 14 micron component, is redirected back into the dermis resulting in an increase in venal stimulation resulting in physiological and behavioral responses. Increasing overall blood flow and improving circulation increases in blood flow to the brain to reduce cerebral hypoperfusion. Cerebral hypoperfusion is simply decreased blood flow to the brain (FIG. 7). There have been numerous studies in the medical literature demonstrating hypoperfusion in children with autism. With newer upgraded brain-imaging cameras, detecting hypoperfusion in children with autism continues to become more defined. The diminished blood flow can be seen with a clear correlation to many core autistic symptoms/behaviors. For example, when the thalamus has hypoperfusion the results are repetitive, self-stimulatory, and unusual behaviors presented by individuals with Autism. Garments of the present disclosure create a unique microenvironment between the skin and the fabric. In this microenvironment, the energy from the body is transmitted by evaporation, convection, radiation, and conduction as noted in FIG. 8.

The temperature of the patient's body is regulated in part by neural feedback mechanisms, which operate primarily through the hypothalamus. The hypothalamus contains not only the control mechanisms, but also key temperature sensors. Under control of these mechanisms, sweating typically begins almost precisely at a skin temperature of 37° C. and increases rapidly as the skin temperature rises above this value. The heat production of the body under these conditions remains almost constant as the skin temperature rises. If the skin temperature drops below 37° C. a variety of responses are initiated to conserve the heat in the body and to increase heat production. These include: vasoconstriction to decrease the flow of heat to the skin; cessation of sweating; shivering to increase heat production in the muscles; and/or secretion of norepinephrine, epinephrine, and thyroxine to increase heat production.

When the ambient temperature is above body temperature, then radiation, conduction and convection all transfer heat into the body rather than out. Since this is generally a net outward heat transfer, mechanisms left under those conditions for cooling include the evaporation of perspiration from the skin and the evaporative cooling from exhaled moisture. Even when one is unaware of perspiration, physiology texts quote an amount of about 600 grams per day of "insensate loss" of moisture from the skin. The cooling effect of perspiration evaporation makes use of the very large heat of vaporization of water. This heat of vaporization is approximately 580 cal/gm at the normal skin temperature.

The basic heat transfer equation for radiation is $$\frac{Q}{t} = e\sigma A(T_{hot}^4 - T_{cold}^4)$$

where A is the area of the human body and e is the emissivity of the skin. In this case, the temperatures are in Kelvin.

Even when inactive, an adult male, for example, loses heat at a rate of about 90 watts as a result of his basal metabolism. This becomes a problem when the ambient temperature is above body temperature, because all three standard heat transfer mechanisms work against this heat loss by transferring heat into the body. One's ability to exist in such conditions comes from the efficiency of cooling by the evaporation of perspiration. At a temperature of 45

Celsius (113 Fahrenheit), the evaporation process must overcome the transfer of heat into the body and give off enough heat to accomplish a 90 watt net outward flow rate of energy. Because of the body's temperature regulation mechanisms, the skin temperature would be expected to rise to 37° C. at which point perspiration is initiated and increases until the evaporation cooling is sufficient to hold the skin at 37° C. if possible. With those assumptions about the temperatures, the Stefan-Boltzmann law for an area of 2 $m^2$ and emissivity 0.97 gives a net radiant input power of 109 watts to the body. The perspiration cooling must overcome that and produce the net outflow of 90 watts for equilibrium. Introducing an implementation of a carbonaceous fiber blend textile material of the present disclosure significantly changes the energy dynamics in the latter condition. First, the radiant protection properties will limit the inbound radiation, decreasing the present demand for perspiration. Secondly, the energy from the micro-environment that exists between the inner textile surface and the outer surface of the skin created by such carbonaceous fiber blend textile material will drive more efficient perspiration evaporation.

In Table 1 below, the net perspiration demand has been theoretically reduced from 207 watts to 102 watts using an implementation of a carbonaceous fiber blend textile material in accordance with the present disclosure. The result is a cooler micro-environment and greater comfort.

TABLE 1

|  | Baseline | Instant Carbonaceous Fiber |
|---|---|---|
| Basal | +90 watts | +90 watts |
| Radiation | +109 watts | +11 watts |
| Convection | +8 watts | +1 watts |
| Perspiration | −207 watts | −102 watts |

One implementation of a carbonaceous fiber blend textile material of the present disclosure includes a relatively high density outer surface, which facilitates the ability of such carbonaceous fiber blend textile material to potentially reflect approximately 90+% of convective and radiant energy. This radiant reflection property limits external radiant energy from penetrating the body as noted above, and, additionally, creates warmth as well by keeping the body's radiant heat in the micro-environment.

In implementations of the present disclosure, fibers have a relatively high percentage of carbon fiber, i.e., 25 weight % to 100 weight %, which is a range exceeding the more typical 1-15 weight %, or, when for anti-static purposes, 1-3 weight %. Additionally, implementations of the present disclosure use a carbonaceous fiber blend that is an insulator and not electrically conductive. In some implementations of a carbonaceous fiber blend textile material of the present disclosure include oxidized polyacrylonitrile fiber (OPF), and in one implementation, the fiber can be Zoltek OX Staple Fiber, sold by Zoltek Corporation of 3101 McKelvey Road, Bridgeton, Mo. 63044, which, from a technical datasheet of Zoltek, are crimped staple fibers and are: "oxidized/stabilized PAN fibers (OPAN) that are inherently fire resistant, thermally stable, exhibit excellent resistance to chemicals and solvents and are electrically conductive." The specifications for Zoltek OX fibers are shown in Table 2 below:

TABLE 2

| Material Property | Standard Density | | | | | High Density |
|---|---|---|---|---|---|---|
| Density | 1.37 g/cm³ (0.0495 lb/in³) | | | | | 1.40 g/cm³ (0.0506 lbs/in³) |
| LOI | 40%+ | | | | | 50%+ |
| Fineness | 1.7 dTex | | 2.2 dTex | | 5.0 dTex | 2.2 dTex |
|  | 1.5 denier | | 2.0 denier | | 4.5 denier | 2.0 denier |
| Length | 60 mm | 50 mm | 60 mm | 74 mm | 80 mm | 60 mm | 70 mm |
|  | 2.3 in | 2.0 in | 2.3 in | 3.0 in | 3.1 in | 2.3 in | 3.0 in |
| Format | Crimp level 7/6 per inch (3.0 per cm) | | | | | |

| Fiber Properties | | Chemical Composition (%) | | Chemical Resistance | |
|---|---|---|---|---|---|
| Density | 1.36 g/cc min. | Carbon Content | 62 | Strong Acids | Good |
| Diameter | 12.5µ (1.7 dTex) | Nitrogen | 21.5 | Weak Acids | Excellent |
| LOI | 40%+ | Oxygen | 12 | Strong Bases | Poor |
| Color | Black | Hydrogen | 4.5 | Weak Bases | Good |
| Resistivity | 8 × 10⁸ ohms-cm | Sodium | <0.1 | Organic Solvents | Excellent |
|  |  | Trace Metals | <0.01 |  |  |

The carbonaceous fiber blend textiles may be incorporated into articles of clothing, blankets, medical products, bedding, upholstery and any other article wherein it is desirable to reflect a substantial portion of the body's radiant energy. The carbonaceous fiber blend textiles of the present disclosure are engineered to naturally engage FIR energy at a therapeutic level, with a clinically significant increase as compared to current performance fabrics.

In certain implementations of carbonaceous fiber blends of textile material of the present disclosure, yarn blends are 35 to 70 weight % OPF (carbonaceous fiber) blended with typical apparel yarns such as nylon, polyester, cotton, modal, Tencel®, rayon, acrylic or combinations of these apparel yarns. In one non-limiting implementation, the material is 35 weight % OPF, 15 weight % Modal, and 50 weight % Pima cotton with 8 weight % Lycra®. In another implementation, fabric of the present disclosure includes 50 weight % OPF, 25 weight % Nylon, and 25 weight % Tencel®. One implementation of needled felt is 70 weight % OPF and 30 weight % polyester.

Implementations of the garments and other articles constructed of carbonaceous fiber blends of textile material of the present disclosure are believed to potentially provide benefits to those with neurological conditions, such as, acquired brain injury, ataxia, brain tumor, dementia, dystonia, epilepsy, functional and dissociative neurological symptoms, meningitis, motor neuron disease (MND), multiple sclerosis (MS), muscular dystrophy, myalgic encephalomyelitis (ME), Parkinson's disease, progressive supranuclear palsy (PSP), Huntington's disease, spina bifida and hydrocephalus, spinal injury, stroke, Tourette Syndrome (TS), and/or transverse myelitis (TM).

Implementations of the garments and other articles constructed of carbonaceous fiber blends of textile material of the present disclosure potentially provide what are believed to be attractive therapeutic clothing for potentially optimizing athletic recovery, reducing pain and inflammation, effectively helping manage the challenges of autism, naturally improving sleep cycles, reducing anxiety, reducing blood pressure, and/or increasing blood flow to the body, improving living with post-traumatic stress syndrome (PTSD).

More specifically, with regard to improving athletic recovery, articles constructed of carbonaceous fiber blends of textile material of the present disclosure potentially increase circulation and metabolic activity, reduce fatigue increasing stamina, accelerate reduction of inflammation, accelerate muscle recovery, help flush toxins, improve temperature regulation, and/or reduce need for pharmaceuticals. And, regarding improving sleep cycles, such articles potentially reduce anxiety, reduce insomnia, lengthen sleep cycles, optimize natural body temperature regulation, reduce inflammation, manage pain, and/or educe need for pharmaceuticals.

Regarding managing the challenges of autism, articles constructed of carbonaceous fiber blends of textile material of the present disclosure are potentially responsible for reduced anxiety and aggression, reduced self-injury and meltdowns, reduced risk of hypo/hyperthermia, reduced inappropriate behaviors, improved sleep, reduced pain, and/or reduced need for pharmaceuticals.

With regard to veterinary applications, articles constructed of carbonaceous fiber blends of textile material of the present disclosure potentially accelerate reduction of inflammation, increase circulation and metabolic activity, reduce stiffness, manage pain, enhance work out recovery time, optimize natural body temperature regulation, reduce the need for pharmaceuticals.

One implementation of the present disclosure includes method for treating a user with a neurological disorder. Such method includes providing a textile article including 5 to 100 weight % carbonaceous fiber and 0 to 75 weight % blending fiber, and at least partially covering the user with the textile article. Further, such method includes absorbing, with the textile article, convective and radiant energy generated by the user and emitting back to the user from the textile article at least 50% of convective and radiant energy received from the use, when the textile article is in proximate contact with the user, resulting in the emitted energy being in the far infrared spectrum, and, wherein the emitted energy provides a therapeutic benefit to the user. Optionally, the carbonaceous fiber of such method may be an oxidized polyacrylonitrile fiber that absorbs convective and radiant energy generated by the user, and responsively emits the absorbed energy in the far infrared spectrum, and, if desired, the oxidized polyacrylonitrile fiber is about 30 to 70 weight %, and the blending fiber is about 30 to 70 weight %.

A further implementation of such method includes the carbonaceous fiber is an oxidized polyacrylonitrile fiber that absorbs convective and radiant energy from an environment, and responsively emits the absorbed energy in the far infrared spectrum.

A further implementation of the present disclosure may include the blending fiber being an apparel fiber comprising polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), or any combination thereof. Another implementation of a method of the present disclosure may further comprise evaporating moisture present between the user and the textile article using the emitted energy, wherein the neurological disorder is autism or wherein the pediatric autism.

Another implementation of the present disclosure includes a method of controlling and reducing net perspiration demand of a user, including the steps of providing a textile article having 25 to 100 weight % carbonaceous fiber and 0 to 75 weight % blending fiber; at least partially covering the user with the textile article; and emitting back to the user from the textile article at least 50% of convective and radiant energy received from the user by the textile article in the form of far infrared energy when the textile article is in proximate contact with the user; and evaporating moisture present between the user and the textile article with the emitted energy. Such method may include the carbonaceous fiber being an oxidized polyacrylonitrile fiber that absorbs convective and radiant energy generated by the user, and responsively emits the generated energy in the far infrared spectrum and/or the carbonaceous fiber being an oxidized polyacrylonitrile fiber that absorbs convective and radiant energy from an environment, and responsively emits the absorbed energy in the far infrared spectrum. Another implementation of a method of controlling and reducing net perspiration demand of a user includes the carbonaceous fiber being an oxidized polymeric fiber and is about 30 to 70 weight %; and the blending fiber is about 30 to 70 weight %.

In another implementation of a method of controlling and reducing net perspiration demand of a user, the blending fiber is an apparel fiber comprising polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), or any combination thereof.

A further implementation of the present disclosure includes a textile article suitable for use in treating a user having a neurological disorder. One such implementation includes a textile article comprising 25 to 100 weight % carbonaceous fiber and 0 to 75 weight % blending fiber. Such textile article could in an implementation include the carbonaceous fiber being an oxidized polyacrylonitrile fiber that absorbs convective and radiant energy generated by the user, and responsively emits the absorbed energy in the far infrared spectrum and/or wherein the carbonaceous fiber is an oxidized polyacrylonitrile fiber that absorbs convective and radiant energy from an environment, and responsively emits the absorbed energy in the far infrared spectrum. In another implementation the textile article includes carbonaceous fiber that is an oxidized polymeric fiber and is about 30 to 70 weight %; and the blending fiber is about 30 to 70 weight %. Optionally, the textile article includes the blending fiber being an apparel fiber comprising polyester, nylon, rayon, lyocell, cellulose, wool, silk, linen, bamboo, m-aramid, p-aramid, modacrylic, novoloid, melamine, regenerated cellulose, polyvinyl chloride, antistatic fiber, poly(p-phenylene benzobisoxazole) (PBO), polybenzimidazole (PBI), polysulphonamide (PSA), or any combination thereof. In a still further implementation, the neurological disorders to be treated with the textile article are autism and/or pediatric autism.

In another implementation, the textile article emits at least 50% of convective and radiant energy absorbed from the user when the textile article is in proximate contact with the user and/or the emitted energy is in the far infrared spectrum. Optionally, the textile article fibers are combinable into yarn and knit, woven, or nonwoven forms, and wherein the textile article has a fabric weight from about 3 oz/yd$^2$ to about 20 oz/yd$^2$.

Although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of treating a user with a neurological disorder selected from a group consisting of acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, Parkinson's disease, progressive supranuclear palsy, Huntington's disease, spina bifida and hydrocephalus, spinal injury, stroke, Tourette Syndrome, transverse myelitis, or any combination thereof, the textile article comprising, comprising:
   providing a textile article comprising:
      30 to 70 weight % carbonaceous fiber;
      30 to 70 weight % apparel fiber selected from a group consisting of polyester, nylon, rayon, lyocell, cellulose, wool, silk, linen, bamboo, regenerated cellulose, modal, elastic polyurethane, or any combination thereof; and
   at least partially covering the user with the textile article by placing the textile article adjacent the user's skin;
   absorbing with the textile article convective and radiant energy generated by the user; and
   emitting back to the user from the textile article at least 50% of convective and radiant energy received from the user when the textile article is adjacent the user's skin, and
   wherein the emitted energy is in the far infrared spectrum.

2. The method of claim 1, wherein the textile article comprises about 32 weight % carbonaceous fiber and the apparel fiber comprises about 46 weight % polyester fiber, about 14 weight % modal fiber, and about 8 weight % elastic polyurethane fiber.

3. The method of claim 1, wherein the textile article comprises about 70 weight % carbonaceous fiber and the apparel fiber comprises about 30 weight % polyester fiber.

4. The method of claim 1, wherein the apparel fiber includes a combination of cotton fiber, modal fiber, and elastic polyurethane fiber, wherein the cotton fiber is a greater weight % than the modal fiber, and the modal fiber is a greater weight % than the elastic polyurethane fiber.

5. The method of claim 1, wherein the apparel fiber includes a combination of lyocell fiber, nylon fiber, and elastic polyurethane fiber.

6. The method of claim 1, wherein the carbonaceous fiber is an oxidized polyacrylonitrile fiber.

7. The method of claim 1, wherein the neurological disorder is epilepsy.

8. The method of claim 1, wherein the carbonaceous fiber is an oxidized polyacrylonitrile fiber that absorbs convective and radiant energy from an environment and responsively emits the absorbed energy in the far infrared spectrum.

9. A method of treating a user with a neurological disorder selected from a group consisting of acquired brain injury, ataxia, brain tumor, dementia, dystonia, epilepsy, functional and dissociative neurological symptoms, meningitis, motor neuron disease, multiple sclerosis, muscular dystrophy, myalgic encephalomyelitis, Parkinson's disease, progressive supranuclear palsy, Huntington's disease, spina bifida and hydrocephalus, spinal injury, stroke, Tourette Syndrome, transverse myelitis, or any combination thereof, the textile article comprising, comprising:
   providing a textile article comprising:
      30 to 50 weight % carbonaceous fiber; and
      50 to 70 weight % blending fiber comprising a combination of polyester fiber, modal fiber, and elastic polyurethane fiber, wherein the polyester fiber is a greater weight % than the modal fiber, and the modal fiber is a greater weight % than the elastic polyurethane fiber; and
   at least partially covering the user with the textile article by placing the textile article adjacent the user's skin;
   absorbing with the textile article convective and radiant energy generated by the user; and
   emitting back to the user from the textile article at least 50% of convective and radiant energy received from the user when the textile article is adjacent the user's skin, and
   wherein the emitted energy is in the far infrared spectrum.

* * * * *

UNITED STATES PATENT AND TRADEMARK OFFICE
CERTIFICATE OF CORRECTION

PATENT NO. : 11,413,185 B2
APPLICATION NO. : 17/135143
DATED : August 16, 2022
INVENTOR(S) : David L. Burge and Catherine M. Burge It is certified that error appears in the above-identified patent and that said Letters Patent is hereby corrected as shown below:

In the Claims

In Claim 1 at Column 15 in Line 29, replace "textile article comprising," with "method".

In Claim 9 at Column 16 in Line 30, replace "textile article comprising," with "method".

Signed and Sealed this
Eighth Day of November, 2022

Katherine Kelly Vidal
*Director of the United States Patent and Trademark Office*